United States Patent
Edwards et al.

(10) Patent No.: US 6,483,247 B2
(45) Date of Patent: Nov. 19, 2002

(54) LIGHTING APPARATUS AND LIGHT CONTROL METHOD

(75) Inventors: Brian R. Edwards, Raymond, ME (US); Walter T. Manchester, Windham, ME (US); Walter C. Hebold, Raymond, ME (US)

(73) Assignee: Syris Scientific, L.L.C., Gray, ME (US)

( * ) Notice: Subject to any disclaimer, the term of this patent is extended or adjusted under 35 U.S.C. 154(b) by 0 days.

(21) Appl. No.: 09/789,686

(22) Filed: Feb. 20, 2001

(65) Prior Publication Data

US 2002/0113560 A1 Aug. 22, 2002

(51) Int. Cl.⁷ ................................................. G06K 7/10
(52) U.S. Cl. .......................... 315/117; 315/291; 315/362
(58) Field of Search ................................ 315/291, 224, 315/307, 308, 360, 362, 112–133

(56) References Cited

U.S. PATENT DOCUMENTS 4,980,900 A  * 12/1990 Welton ........................ 315/360
6,333,602 B1 * 12/2001 Kayser ........................ 315/117

* cited by examiner

*Primary Examiner*—Don Wong
*Assistant Examiner*—Wilson Lee
(74) *Attorney, Agent, or Firm*—Michael J. Persson; Lawson, Philpot & Persson, P.C.

(57) ABSTRACT

A lighting apparatus and method. The apparatus includes a light source, counting means for counting an actual amount of time that the light source has been used, and recording means in communication with the counting means for recording the actual amount of time that the light source has been used. The method includes the steps of supplying power to the light source, counting an actual amount of time that the power has been supplied to the light source, and recording the actual amount of time that power has been supplied to the light source.

18 Claims, 6 Drawing Sheets

LIGHTING APPARATUS AND LIGHT CONTROL METHOD

FIELD OF THE INVENTION

The present invention relates to the field of lighting and, in particular, to a light apparatus having a light control, and method for tracking the usage of a light and providing information relating to such use.

BACKGROUND OF THE INVENTION

The assignee of the present invention manufactures and sells vision enhancement systems falling within the scope of U.S. Pat. No. 5,742,392, which is incorporated herein by reference. These systems generally include an illuminator made up of a housing and a plurality of illuminator elements disposed within the housing. These illuminator elements are a light source, a first polarizer, a lens, an aperture, an optical filter, a viewing means, and a headgear system, which allows the illuminator to be worn on the head of a user. The viewing means includes a second polarizer having a second plane of polarization, which is rotationally positionable with respect to the first polarizer such that their respective planes of polarization may be aligned in either a parallel or orthogonal relationship.

The systems described above are typically used by dermatologists, aesthetic laser surgeons and phlebologists during examinations and procedures performed on patients and has become an essential instrument for the practice of many of these professionals. As this is the case, the failure of these systems can prevent these professionals from performing their duties, resulting in significant inconvenience for patients and significant loss of revenue for the professional.

Given the problems caused by system failures and fact that the most common component to fail is the bulb, one apparent solution would be for the professional to keep a spare bulb on-hand in the event that the bulb unexpectedly fails. However, in order to meet space and weight requirements in these systems, the illuminators include a bulb assembly that has an integral microcontroller and fan unit. Accordingly, the bulb itself is not separately replaceable and the entire illuminator must be replaced when the bulb fails. Given the relatively high cost of illuminators, keeping a spare is an unattractive option to most professionals. Thus, there is a need for a way to alert users of the system when a bulb failure is imminent, so that the user may order a new illuminator for delivery just before the time when the bulb fails.

The relatively high cost of illuminators has also lead to warranty concerns on the part of the manufacturer. The life of a bulb is directly related to a number of factors, including the temperature of the bulb, the thermal and electrical transients produced at startup, the amount of power supplied to the bulb, physical abuse, etc. However, the primary factor in the life of a bulb is the number of hours of bulb use. Typically, the manufacturer of these systems knows this expected life of the bulb, but has no way of knowing the level of actual usage made of the bulb. Therefore, the manufacturer either had to place an arbitrary time frame upon the warranty period, i.e. six months, one year, etc., or had to rely upon the recollection, and honesty, of the professionals with respect to the actual use of the lamps. Thus, there is also a need for the manufacturer to effectively determine how many hours that a bulb has been used once it has been submitted to the manufacturer for warranty replacement.

Finally, although the life of a bulb is primarily dependent upon the number of hours used, as noted above, the temperature of the bulb, transients produced at startup, and overall power to the bulb also contribute to this life. Therefore, there is a need to control these factors in order to insure that the bulb will not prematurely fail due to overheating, to protect the bulb from power and thermal transients during startup, and to reduce the overall power to the bulb when the bulb is nearing the end of its useful life.

A number of United States Patents have issued addressing one or more of these issues. However, none are adapted to effectively solve the problems addressed by the present invention. For example, U.S. Pat. No. 4,876,632 discloses a battery life indicator for a flashlight. The preferred indicator is a series of three LED's that receive signals from a life measurement circuit and indicate a corresponding level of battery charge. Although the user of this apparatus is appraised of when a battery failure is imminent, it does not keep track of the length of use. Accordingly, its function is analogous to a fuel gauge in an automobile, while the present need is for something analogous to an odometer.

U.S. Pat. No. 6,039,462 discloses a light unit having a thermal fuse. Once the maximum temperature of the light is exceeded, the fuse is triggered and the circuit is broken, effectively ceasing the flow of power to the light. Such a system is effective as a safety device, to prevent an overheated light from causing a fire. However, it is not adapted to the present invention as the thermal fuse will have the same effect as a burned bulb; i.e. will cause the illuminator to cease working and require replacement.

U.S. Pat. No. 4,888,678 discloses a light socket that utilizes a thermistor as a means for effecting a "soft-start". Here the thermistor is a negative temperature coefficient type connected in series with rectifier. The thermistor preferably has an R value at 250 degree C. of between 10 and 100 ohms, while its R at 75 degrees C. is considerably less. The thermistor has a preferred power dissipation of under two watts and a soft glow time from zero to maximum brightness of 1–3 seconds. The presence of a thermistor is said to help to extend a bulb's life and is particularly desirable if the light bulb with which the socket adapter is used is turned on-and-off somewhat frequently as it affects the stress the bulb encounters when the initial rush of current occurs. Although this device is helpful at solving the problem of thermal transients at power-up, it is not readily adapted to provide protection against overheating during operation.

U.S. Pat. Nos. 5,684,366, 5,683,246, 5,267,857, 4,929,872, 4,360,743, 4,238,709, 4,037,135, 4,008,416, 3,963,956, and 3,952,242, each describe lamps, or other devices, utilizing a soft-start feature that reduces electrical and thermal transients by slowly powering-up the device. Although each of these devices is helpful at solving the problem of thermal and electrical transients at power-up, none are readily adapted to provide protection against overheating during operation and none are adapted to reduce the final intensity of power to the device when it is nearing the end of its useful life. Therefore, there is a need for a lamp having a means for continuous accumulating total run time, means for using this information for displaying lamp life information to the user, means for temporarily removing power from the bulb when the lamp is overheated, means for lowering lamp intensity once it has reached a certain number of hours of use, and a "soft start" feature for reducing thermal and electrical transients during start-up.

SUMMARY OF THE INVENTION

The present invention is a lighting apparatus and lighting method that overcome the drawbacks of current systems. In its most basic form, the lighting apparatus of the present invention includes a light source, counting means for counting an actual amount of time that the light source has been used, and recording means in communication with the counting means for recording the actual amount of time that the light source has been used.

In the preferred embodiment, the apparatus includes a microcontroller that includes a microprocessor, a computer memory and input/output ports. A counting program is programmed into the microprocessor of the microcontroller to serve as the counting means, while the computer memory acts as the recording means. The preferred microcontroller is also programmed to compare the actual amount of time that the light source has been used with a predetermined amount of time.

The preferred apparatus also includes a display, which in communication with the microcontroller and is adapted to display the actual amount of time that the light source has been used. The preferred display is a series of three indicator lights that correspond to a number of hundreds of hours, a number of tens of hours and a number of single hours. These indicator lights receive corresponding signals from the microcontroller and are illuminated once for each signal to indicate the number of hours that the apparatus has been used. In some embodiments, however, the display is at least one indicator light that receives a number of signals from the microcontroller corresponding to a number of hours that the light source has been and is illuminated upon receipt of each of the signals. In still other embodiments, at least one indicator light is illuminated when the microcontroller sends a signal indicating that the amount of time exceeds the predetermined amount of time.

The preferred apparatus also includes a light source control for controlling a supply of power to the light source and a temperature measurement device for measuring a temperature of the apparatus. The temperature measurement device is in electrical communication with the light source control, which is adapted to control a supply of power to the light source based upon the temperature of the apparatus. It is preferred that the light source control be a light source control program within the microcontroller, which is adapted to stop a supply of power to the light source when the temperature exceeds a predetermined temperature and start a supply of power to the light source after the apparatus is stopped and restarted. In some embodiments, the temperature measurement device is omitted and the light source control controls the power to the light source based upon the information received from the microcontroller. In some such embodiments, the microcontroller is further programmed to compare the actual amount of time that the light source has been used with a useful life of the light source and to send a signal to the light source control to supply a reduced amount of power to the light source when the actual amount of time exceeds the useful life of the light source. In other embodiments, the microcontroller is programmed to compare the actual amount of time that the light source has been used with a predetermined amount of time and to send a signal to the light source control to oscillate the power to the light once the actual amount of time exceeds the predetermined amount of time. In still other embodiments, the microcontroller is programmed to compare the actual amount of time that the light source has been used with a purchased life of the apparatus and to send a signal to the light source control to prevent a flow of power to the light source when the actual amount of time exceeds the a purchased life of the apparatus.

In its most basic form, the lighting method includes the steps of supplying power to the light source, counting an actual amount of time that the power has been supplied to the light source, and recording the actual amount of time that power has been supplied to the light source.

The preferred method also includes the steps of displaying the actual amount of time that the power has been supplied to the light source, comparing the actual amount of time that the power has been supplied to the light source with a predetermined amount of time, and providing an alert when the actual amount of time that the power has been supplied to the light source exceeds the predetermined amount of time.

It is also preferred that the method include the steps of controlling the supply of power to the light source based upon a result of the comparing step. In some embodiments, the predetermined amount of time is a purchased life of the light source and the controlling step includes the step of preventing a flow of power to the light source when the actual amount of time exceeds the purchased life of the apparatus. In other embodiments, the predetermined amount of time is a useful life of the light source and the controlling step includes the step of reducing a flow of power to the light source when the actual amount of time exceeds the a useful life of the apparatus.

Finally, the preferred method includes the steps of measuring a temperature of the apparatus and controlling the supply of power to the light source based upon a result of the measuring step.

Therefore, it is an aspect of the invention to provide a light apparatus and method that continuously accumulate the total run time of the light source.

It is a further aspect of the invention to provide a light apparatus and method that display lamp life information to the user.

It is a further aspect of the invention to provide a light apparatus and method that temporarily remove power from the light source when the lamp is overheated.

It is a further aspect of the invention to provide a light apparatus and method that lower lamp intensity once the lamp has reached a certain number of hours of use.

It is a further aspect of the invention to provide a light apparatus and method that include a "soft start" feature for reducing thermal and electrical stresses during start-up.

It is a further aspect of the invention to provide a light apparatus and method that allow a user to purchase a certain number of hours of use and will prevent power from being sent to the light source once that number of hours has elapsed.

It is a further aspect of the invention to provide a light apparatus and method that oscillate the power to the light source once the actual amount of time exceeds the predetermined amount of time in order to alert the user to an impending failure of the light source.

It is a still further aspect of the invention to provide a light apparatus and method that illuminates an indicator light once it has reached a certain number of hours of use.

These aspects of the invention are not meant to be exclusive and other features, aspects, and advantages of the present invention will be readily apparent to those of ordinary skill in the art when read in conjunction with the following description, appended claims and accompanying drawings.

DETAILED DESCRIPTION OF THE INVENTION

Figure 1:
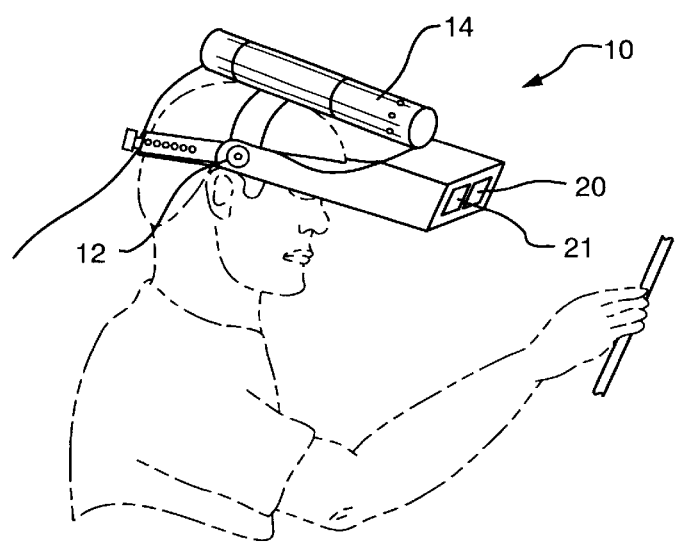
FIG. 1 is an isometric view of a user wearing a prior art polarized material inspection apparatus.

The preferred lighting apparatus of the present invention includes many of the basic elements of the polarized material inspection apparatus disclosed in U.S. Pat. No. 5,742, 392. As shown in FIG. 1, the prior art lighting apparatus is adapted to be worn upon the head of a user and includes a device 10 for object or material analysis includes a support means 12 and a illuminator 14.

Figure 2:
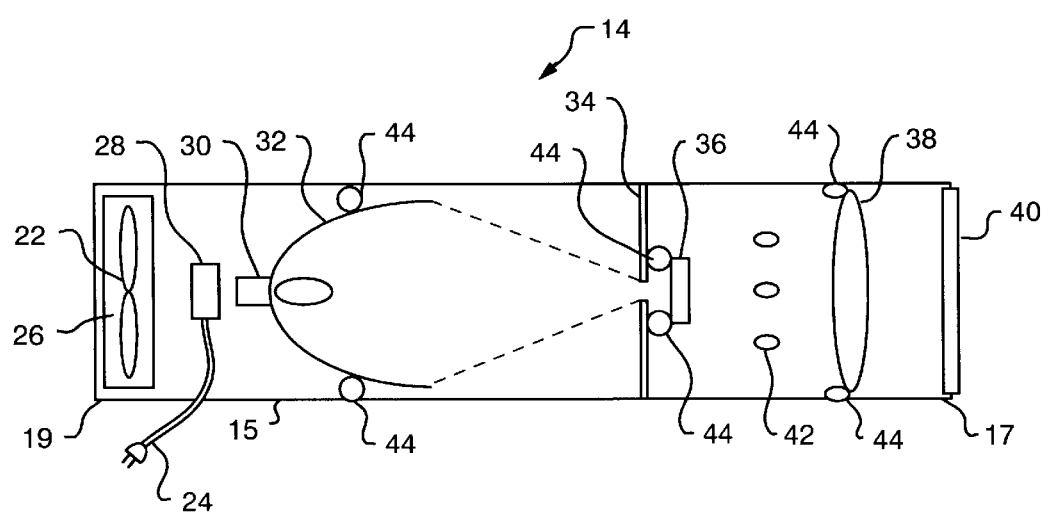
FIG. 2 is a cut away side view of an illuminator that is part of the prior art polarized material inspection apparatus of FIG. 1.

As shown in FIG. 2, the illuminator 14 incorporates a plurality of elements, which in concert provide substantially uniform polarized light to irradiate a site of interest. The illuminator 14 includes a housing 15 having a first end 17 and a second end 19, which forms an optical path and houses the illuminator elements. The preferred orientation is positioning the first end 17 so that it is closer to the filters 20 and 21 than the second end 19. A power supply means 24 connects to the internal components of the housing 15 to supply power to the system's components requiring the same.

A light source 30 is used to provide light to illuminate the object or material to be inspected. The light source 30 is located inside a reflector 32, preferably at its focus.

The reflector 32 typically has an smooth elliptical shape, opening out such that the light reflected from the elliptical shape is directed down the optical path formed by the structure of the housing 15. The reflected light is focused by reflector 32 at an aperture 34. The focused light passes through aperture 34 and an infrared blocking, visible light passing filter 36. However, some embodiments of the invention utilize a dichroic reflector 32 that reflects only ultraviolet radiation in the visible spectrum and passes infrared, i.e. heat, back through the rear of the unit. In these embodiments, infrared blocking, visible light passing filter 36 is unnecessary and is eliminated.

A number of elements that can be chosen as the light source 30. These include, but are not limited to, incandescent lamps, tungsten-halogen lamps, various bulbs and filament arrangements. The use of polarizers (see below) limits the total visible light to only about 1/10 of that occurring without the polarizers. Therefore, a bright light source is needed. However, a typical light source 30 having the required intensity generates a vast amount of heat, typically 20–40 watts. Since the light source 30 is confined inside the housing 15, the heat needs a way to be dissipated. Therefore, in order to dissipate the heat generated by the light source 30, a cooling means 26 is located within the housing 15 at the second end 19 thereof.

The cooling means 26, which is used to dissipate the heat generated by the light source 30, is a convection cooling means, which includes an exhaust fan 22. The exhaust fan 27. provides sufficient convective cooling to the illuminator components located within the housing by drawing cooler air from outside the illuminator 14 into the interior of housing 15. The air is drawn into and then out of the device via the exhaust fan 26. The exhaust fan 26 is incorporated into the system to extend the device's 10 useful life. Further, by maintaining the device 10 at a moderate temperature, a user can handle the device 10 safely and without the need for special protection from burn injuries, such as protective gloves, or the like.

The power adapting means 28 can be a switching device, AC/DC converter, battery, or the like. Further, it should be recognized that the power adapting means 28 is also electrically connected (not shown) to the light source 30.

In embodiments where a non-dichroic reflector 32 is used, the infrared filter 36 may be used to attenuate infrared light that is generated by the light source 30. If too much infrared light is directed at the object or material of interest for a prolonged period of time, unwanted heating and/or damage can occur to the surface. As indicated above, elliptical reflector 32 is selected to focus a beam of light at aperture 34 such that the light passing through aperture 34 is substantially uniform throughout the cross-section of aperture 34. Lens 38 is then used to project a real image of aperture 34 onto the object to be inspected resulting in a substantially uniform, bright spot of illumination. The spacing between lens 38 and aperture 34 is selected to produce a conjugate ratio to project a magnified image of the aperture onto an object, for example, skin, at a working distance. The working distance is substantially a distance from lens 38 equal to the focal plane of polarized filters 20 and 22.

A first polarizing means 40 is located at an end of the housing. The polarizing means 40 is a linearly polarizing lens that polarizes the light from the light source 30 in a single plane of polarization. This allows for polarized light to irradiate the object or material of interest, as shown in FIG. 1. The polarizing lens 40 is rotatable to any position in between a first position and a second position. By rotating the polarizing lens 40, different planes of polarization can be achieved.

The reflector 32, infrared filter 36 and lens 38 are all spatially maintained in the to system via a plurality of attachment means 44. The plurality of attachment means 44 maintain each of the respective elements in the optical path but with minimal contact with the housing 15 to limit conductive heating of the housing, and to allow for the air flowing within the housing to ventilate and cool the elements. Further, this provides for a more efficient cooling of the air in the system and cooling of the individual elements.

The attachment means 44 are typically adhesive spacers that maintain the elements in a desired orientation and relative position while allowing gaps 45 for flowing air to pass by. Though adhesive spacers 44 have been disclosed as the attachment means, other types of attachment and spacing means could be used. This includes welding, soldering and other mechanical joining means being use to adhere the elements to their respective surfaces, and clamps which grasp the elements of the housing while allowing air to flow therethrough.

In operation, the illuminator 14 irradiates the surface with linearly polarized light generated by light passing through the first polarizer 40 oriented in a first position. The backscattered light is detected by a user via a second set of fixed polarized filters 20 and 22 and magnifying lenses 20 and 22. In the first position, the plane of polarization of the first polarizer 40 is parallel to the plane of polarization of filters 20 and 22. Thus, the light reflected from the surface allows the user to view surface properties. By rotating either the first polarizer 40 or the polarized filters 20 and 22 to a second position ninety degrees from the first, perpendicular axes of polarization are formed between the first polarizer 40 and the polarized filters 20 and 22. This allows the user to view subsurface features of the skin, tissue or other material to be inspected.

The change between the incident and detected planes from parallel to perpendicular is caused by the rotation of the polarizer 40 from one position to another and preferably from a first, predetermined position to a second, predetermined position. The total amount of rotation between the first and second predetermined positions is 90 degrees. The user can also choose to vary the amount of rejection of surface reflectance by selectively adjusting the polarizers intermediate their first and second predetermined positions.

The light apparatus of the present invention may include the same optical elements as the illuminator 14 of the prior art device 10 and may be a single unit that combines both the illuminator and optics. However, the preferred light apparatus has been modified to include an illuminator module that attaches to an optical module, which houses the optical elements of the apparatus. Accordingly, when the light source 30 of the preferred lighting apparatus reaches the end of its useful life, the user needs only replace the illuminator module rather than replacing the entire illuminator 14, including the optics. This is advantageous as it results in a significant cost savings to the user.

Figure 3:
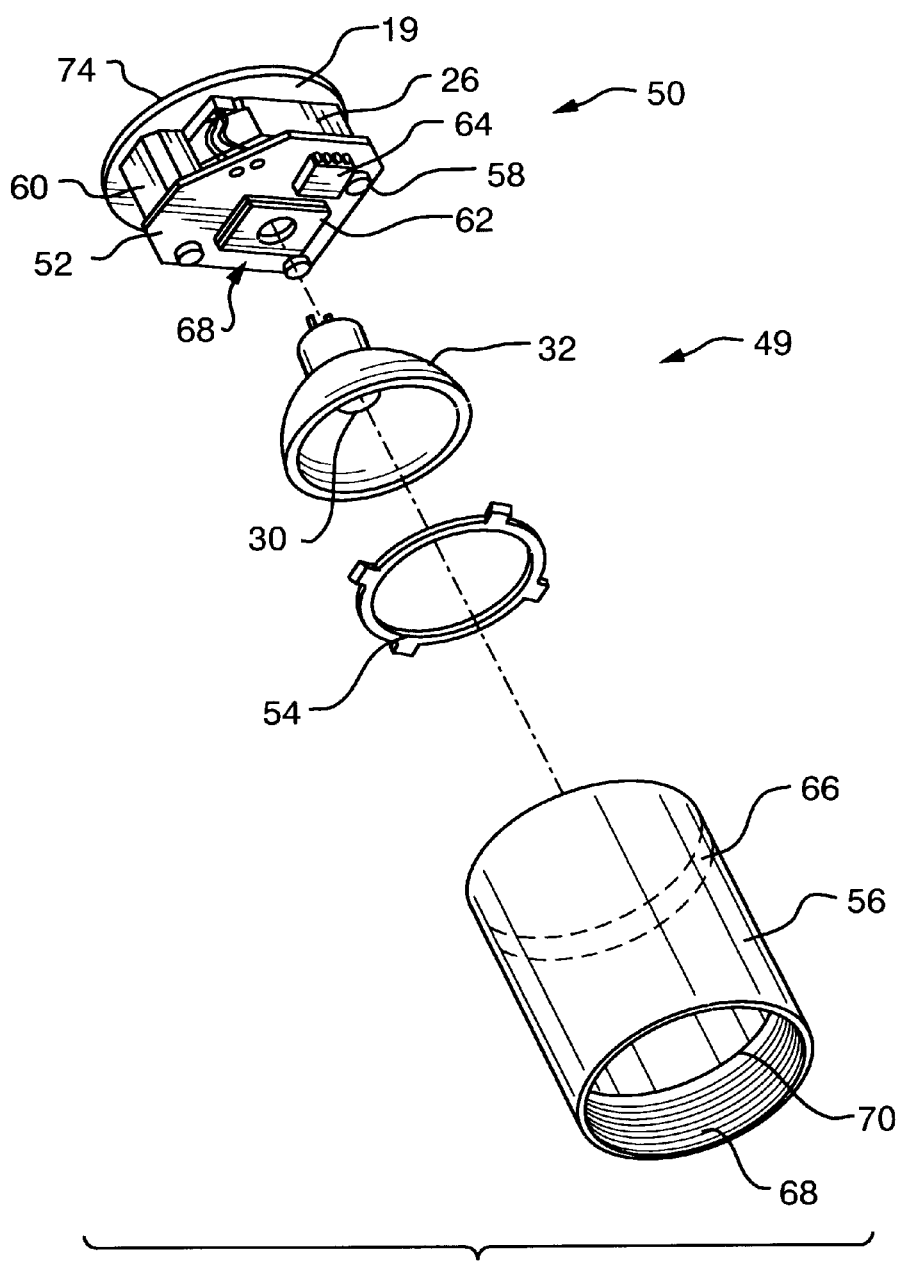
FIG. 3 is an exploded view of the illumination module of the preferred lighting apparatus.

As shown in FIG. 3, the illuminator module 49 includes a printed circuit board assembly 50, a light source 30, a retaining ring 54 and a hollow cylindrical housing 56 into which the other components 50, 30, 34 are disposed. The printed circuit board assembly 50 includes the second end 19 of the housing 56, a fan 26, and a printed circuit board 52. These components 56, 26, 52 are preferably secured together by three screws 58 that are dimensioned to pass through holes in the printed circuit board 52 and fan 26 and mate with threaded holes in the second end 19 of the housing 56.

The housing 56 includes internal threads 66, 68 at each end and an internal flange 70 at one end. The internal flange 70 is dimensioned to accept the retaining ring 56, which holds the reflector 32 of the light source 30 into position. During assembly, the retaining ring 56 is seated upon the internal flange 70. The assembled printed circuit board assembly 50 is then secured to the housing 56 by threading the male threads 74 on the outside edge of the second end 19 to the female threads 66 on the inside of the housing 56 until the reflector 32 of the light source 30 comes into contact with the internal flange 70.

A plurality of electrical components, including a power input 60, a light socket 62, and a microcontroller 64 are mounted to the printed circuit board 52. The power input 60 is dimensioned to bridge the space between the printed circuit board 52 and the second end 19 of the housing 56 at a location adjacent to the fan 26. In the preferred embodiment, the power input 60 is dimensioned to accept a removable DC power cable (not shown) and is positioned to mate with a corresponding opening 76 in the second end 19 of the housing 56. However, in other embodiments, the power input 60 is attached to a fixed power cable via soldering or mechanical connection.

The light socket 56 is dimensioned to accept the light source 30, while leaving sufficient space on the back side 68 of the printed circuit board 52 for mounting the microcontroller 64. The light socket 56 preferably includes an opening for securing the reflector 32 in such a manner as to allow light from the light source 30 to be reflected.

The microcontroller 64 is preferably a CMOS microcontroller having a microprocessor unit, an internal oscillator, a counter, an analog to digital converter, and an EEPROM data memory. In this preferred embodiment, the microcontroller 64 serves both as the counting means and as the recording means, with the real counter counting the actual time that the apparatus is used and the EEPROM accepting updates from the counter. In other embodiments, the microcontroller is eliminated and a separate microprocessor and memory device serve as the counting means and the recording means. In others, the microcontroller is replaced with a basic counting circuit, which sends a signal to a recording means, such as a computer memory or electromechanical counter. Finally, in still other embodiments, an electromechanical clock and counter serve as the counting means and recording means.

Figure 4:
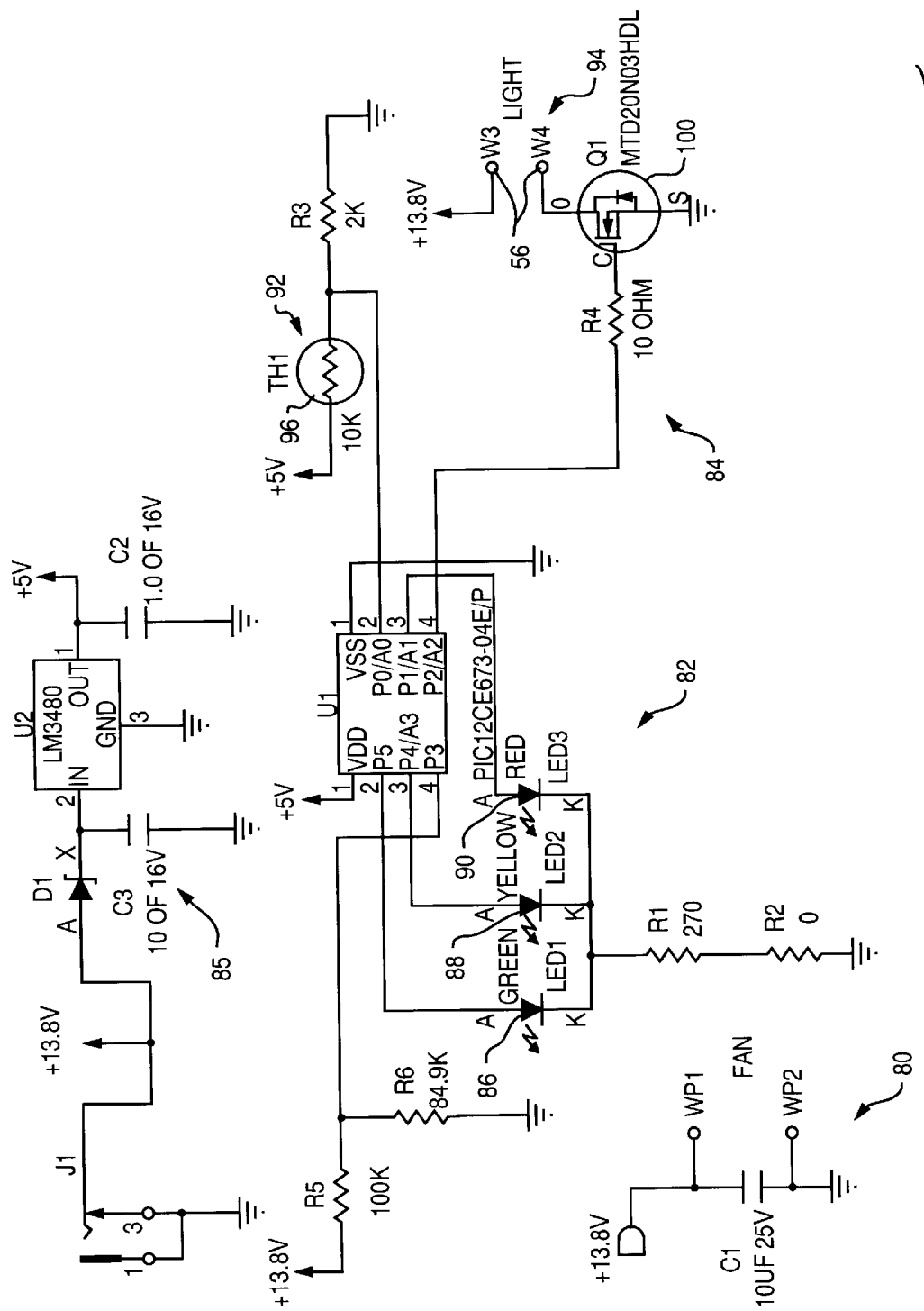
FIG. 4 is a circuit diagram of the preferred printed circuit board.

FIG. 4 is a circuit diagram showing the layout of the preferred printed circuit board 52. The preferred printed circuit board 52 includes a fan circuit 80, an indicator light circuit 82, and a light control circuit 84, and a voltage regulation circuit 85.

The voltage regulation circuit 85 is adapted to accept power at 13.8 volts and step that voltage down to the 5-volt power required by the microcontroller 64. However, it is recognized that this voltage regulation circuit 85 may be altered or eliminated based upon the voltage requirements of different embodiments of the invention. The fan circuit 80 is a separate circuit, which simply accepts power from the power input 60 and provides power to the fan 26. The indictor light circuit 82 and light control circuit 84 each include, and are controlled by, the microcontroller 64.

The preferred indicator light circuit 82 includes connections from the microcontroller 64 to three light emitting diodes, or LED, 86, 88, 90, each of a different color. In the preferred apparatus, the first LED 86 is a green LED, the second LED 88 is a yellow LED, and the third LED 90 is a red LED. As described more fully below with reference to the method of the present invention, these diodes are each illuminated upon receipt of a signal from the microcontroller 64.

The preferred light control circuit 84 includes two sub circuits 92, 94, each connected to the microcontroller. The first sub-circuit is the temperature sending circuit 92. This circuit 92 includes a thermistor 96, which measures the temperature inside of the housing and sends a signal to the microcontroller corresponding to that temperature. The second sub-circuit is a power control circuit 94. The preferred sub circuit 94 the switch 100 is a transistor that is adapted to accept a pulse width modulated (PWM) signal from the microcontroller 64 and to send a variable voltage to the light socket 56 based upon these signals. However, it is recognized that other switches 100, such as mechanical or solid state relays, or the like, may be utilized to achieve similar results.

Figure 5:
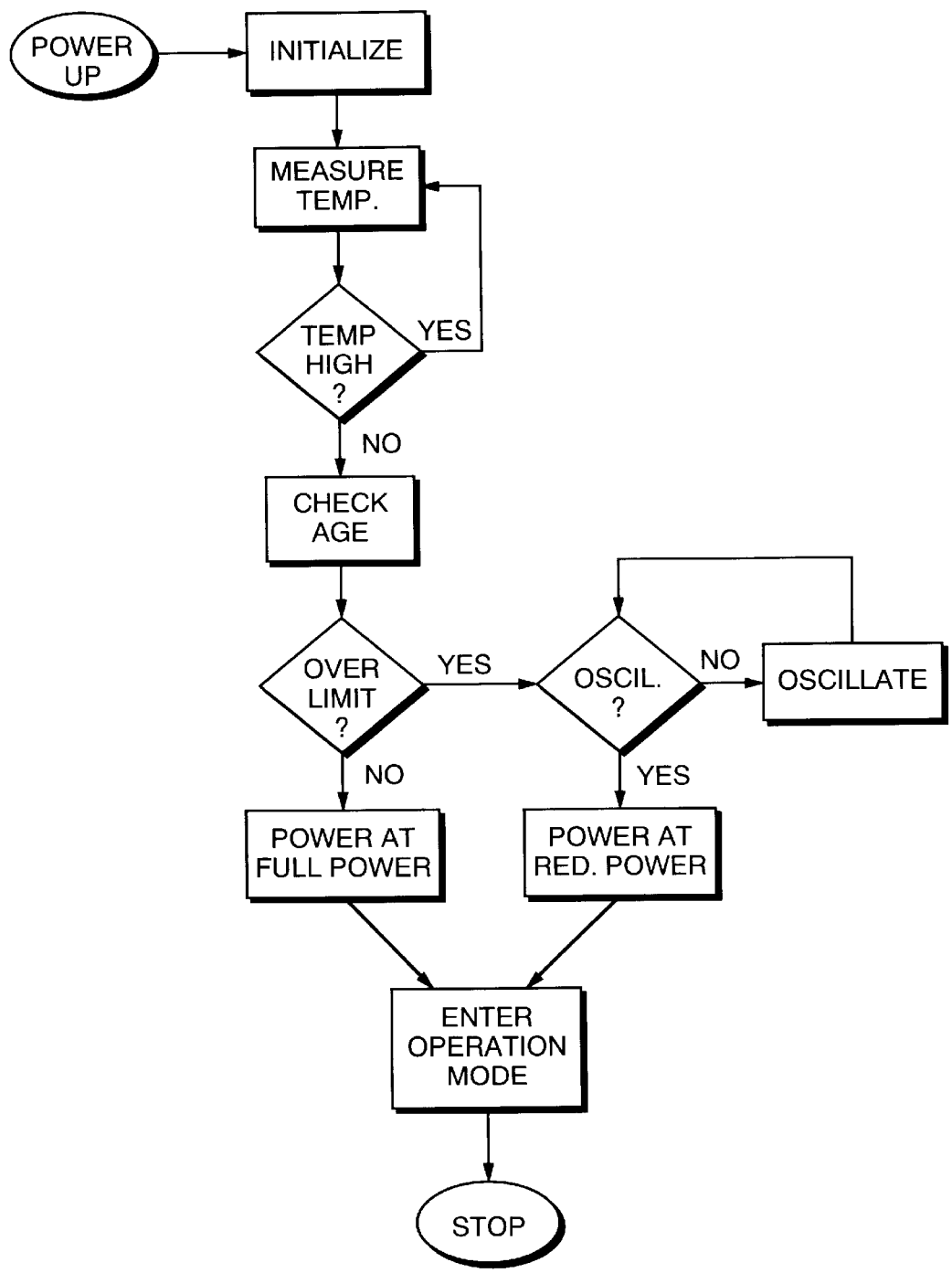
FIG. 5 is a flowchart showing the start-up steps method of the present invention.
Figure 6:
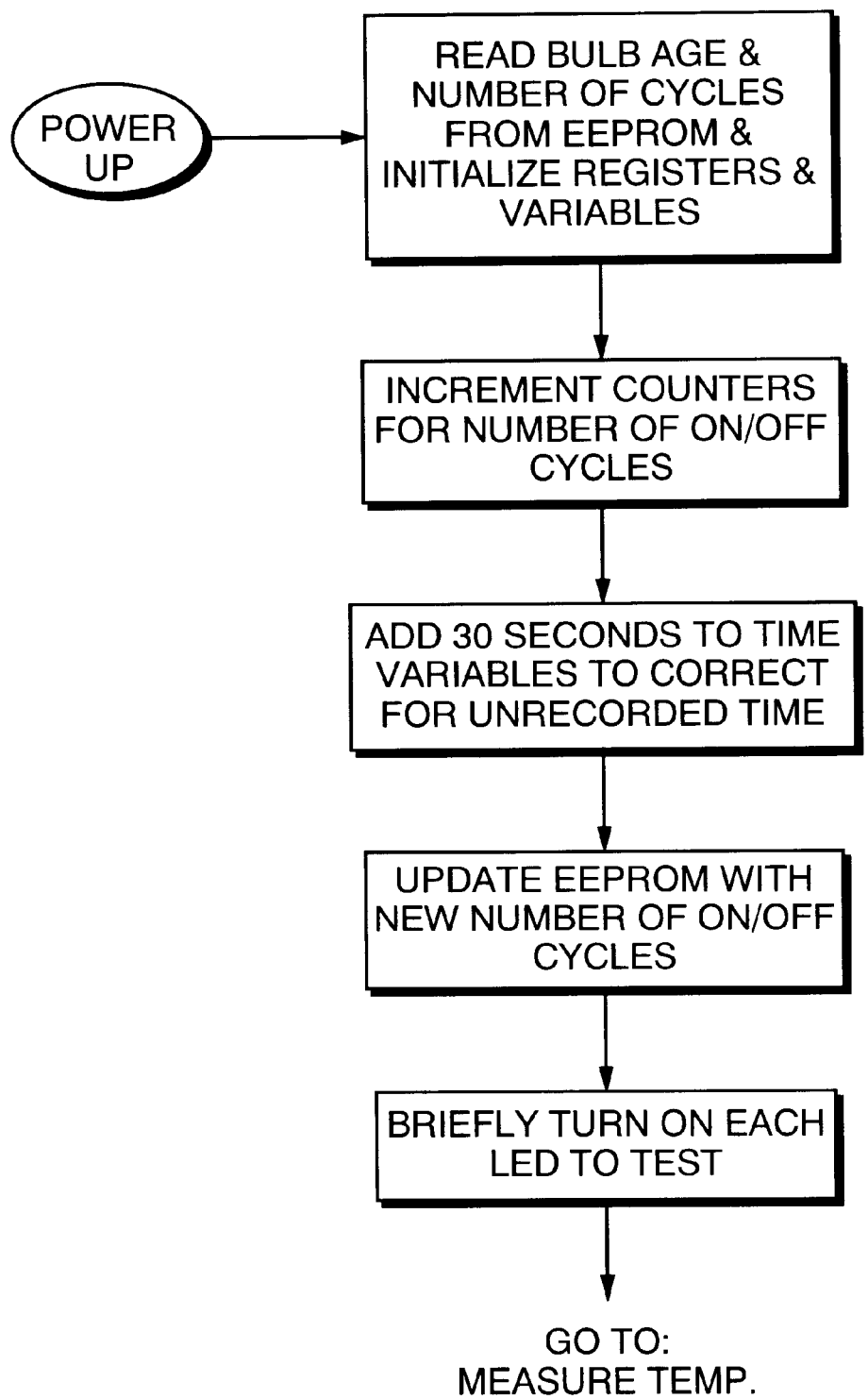
FIG. 6 is a flowchart showing the initialization steps method of the present invention.

The method performed by the preferred apparatus is described with reference to FIGS. 5–7. As shown in FIG. 5, once the unit is powered up, it performs an initialization routine. The flowchart for this initialization routine is shown in FIG. 6. This routine beings by reading the age of the light source, in number of actual hours, and number of on/off cycles recorded by the EEPROM, and initializing the registers and variables within the microcontroller based upon this reading. The counters are then incremented by one to reflect the addition of an on/off cycle. The microcontroller then adds thirty seconds to the time variables to correct for unrecorded time. This step is a compromise in order to allow the EEPROM to be updated once every minute rather than more frequently, which would overstress the memory capabilities of the preferred EEPROM. By adding thirty seconds to the time variables, the potential error associated with this practice is cut from a potential error of plus of minus one-minute error to a potential error of plus or minus thirty seconds. However, over many on-off cycles, the positive and negative errors should substantially cancel each other out, resulting in a fairly accurate measure of time. The EEPROM is then updated with the new number of on/off cycles, as already incremented within the counters. Finally, the LED's are tested by energizing each briefly.

Referring again to FIG. 5, once the initialization routing is performed, the temperature of the unit is measured and the result of this temperature measurement is read by the microcontroller. The microcontroller compares this result with a predetermined maximum temperature to determine whether the temperature is too high. If the temperature is too high, the unit continues to measure temperature and will not move forward with powering the light source or counting the actual run time. The maximum temperature is preferably determined using empirical data for the particular light and housing used.

If the temperature is acceptable, the microcontroller then takes the corrected age of the unit from the EEPROM, in numbers of hours, and compares this value with a predetermined limit. In the preferred embodiment, this limit is a useful life of the light source. However, in other embodiments this predetermined limit is a purchased life agreed upon by the user and the manufacturer. Accordingly, a user would be able to purchase a unit with a shorter life at one price and one with a longer life at a higher price. In these embodiments, once this purchased life is exceeded, the microcontroller completely prevents powering of the light source.

In the preferred embodiment, if the age of the unit does not exceed the predetermined limit, the light source is powered at full power and the apparatus enters operation mode where it runs until turned off by the user. If the age of the unit exceeds the predetermined limit, the microcontroller determines whether the power to the bulb has been oscillated. if not, then power to the bulb is oscillated for a brief period in order to alert the user to the fact that the light source is at the end of its useful life and that a new illuminator module should be purchased. In some embodiments, one or more of the indicator lights is also illuminated in order to provide an additional alert to the user. In others, the oscillation step is completely eliminated and the illumination of the indicator light is the sole means of alert. In still others, no alert is provided to the user. Once power to the light source has been oscillated, the light source is powered at reduced power in order to conserve bulb life and the apparatus enters operation mode where it runs until turned off by the user.

Figure 7:
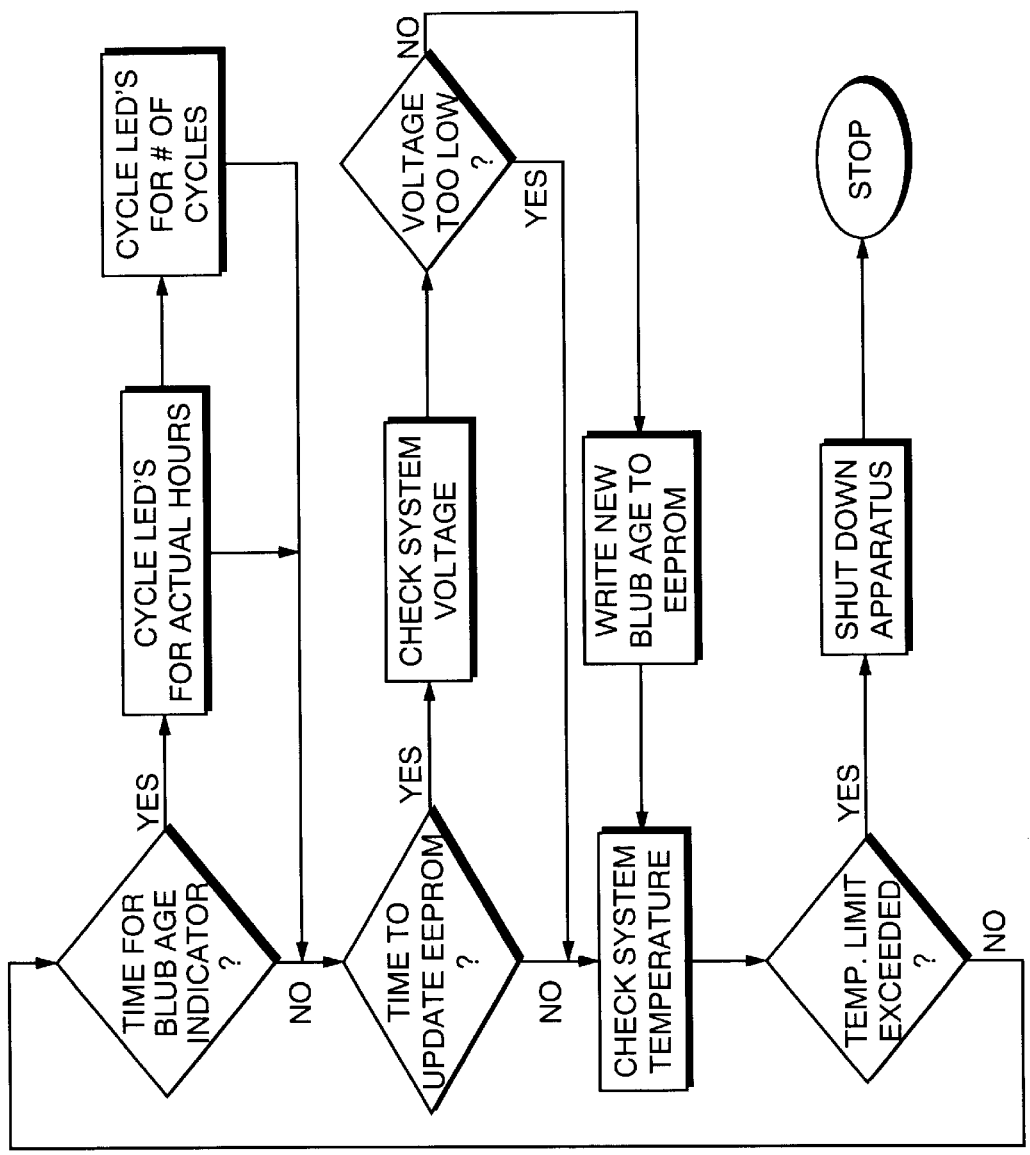
FIG. 7 is a flowchart showing the steps of the method of the present invention performed in operation mode.

Referring now to FIG. 7, a flowchart showing the operation mode of the apparatus is shown. Once operation mode has been entered, the microcontroller determines whether it is time to display the age of the light source. In the preferred embodiment, the time to display the age is approximately twenty seconds after entry into operation mode and, once it has been displayed at this time, the age is not displayed again until the unit is shut down and repowered. However, it is understood that other embodiments may periodically display the age, while others may continuously display the age. if it is time for the age to be displayed, the microcontroller will cycle the LED's to show the actual number of hours that the apparatus has been used and will cycle the LED's for the number of cycles. As noted above, the preferred display is a series of three different colored LED indicator lights, which correspond to a number of hundreds of hours, a number of tens of hours and a number of single hours. The indicator lights receive corresponding signals from the microprocessor and are illuminated once for each signal to indicate the number of hours that the apparatus has been used. In some embodiments, however, the display is a single indicator light that receives a number of signals from the microprocessor corresponding to a number of hours that the light source has been and is illuminated, while in others two such lights are used. In still other embodiments, the indicator lights are eliminated and this step is omitted. Finally, in other embodiments, the indicator lights are replaced with a liquid crystal, or other display, which continuously displays the actual number of hours used.

The microcontroller then determines whether it is time to update the EEPROM. As noted above, it is preferred that the microcontroller keep track of the actual run time and update the age of the unit once every minute. However, it is recognized that this time is dependent upon the particular application and recording means that is utilized and, therefore, in other embodiments the time for updating may be more frequent or less frequent than once per minute.

If it is time to update the EEPROM, the microcontroller checks the system voltage to determine whether it is below a predetermined threshold, below which the data stored within EEPROM may be corrupted if it attempts to write to it. If the system voltage is too low, the microcontroller will not update the EEPROM and the microcontroller will continue with its routine. It is understood that this may produce an error in the actual bulb life recorded in the EEPROM, but such an error is acceptable when weighed against the risk of losing all historical data. If the system voltage is above the threshold, the microcontroller updates the EEPROM.

Finally, the microcontroller again checks the system temperature to determine whether it has exceeded the predetermined threshold. If it has not exceeded the threshold, the microcontroller returns to the start of the operation program and begins the routine once again. If it has exceeded the threshold, the microcontroller shuts down power to the apparatus. Such a complete shut down is preferred as exceeding the temperature threshold is usually the result of a blockage in the flow of cooling air flow by an object, such as a towel, blanket or item of clothing, and does not occur while performing its intended use. However, it is understood that in some embodiments the unit will not be shut down, but rather the power to the bulb will be suppressed until temperature falls back below the threshold. In others, the power to the bulb will be cut back in proportion to the amount of over temperature. In still others, there is no control based upon temperature measurement, but rather a thermal fuse is utilized to prevent the unit from overheating and starting a fire.

It is understood that, although the light apparatus and method have been described with reference to lights for use by medical professions, the light apparatus and method may be readily adapted for use with any light source. For example, it is easily adapted for use in projectors, such as those used to show movies, slides or overheads. It may also be integrated into onboard computer systems for automobiles, boats, airplanes, and the like in order to monitor headlamp, running lamps or the like. It is also envisioned that the system is easily adapted for use in connection with studio photography lights, electroluminescent and fluorescent backlit displays, or with any other illumination source having a finite and predictable life. Therefore, the spirit and scope of the appended claims should not be limited to the description of the preferred versions contained herein.

What is claimed is:

1. A lighting apparatus comprising:

a light source;

a microcontroller;

counting means comprising a counting program within said microcontroller for counting an actual amount of time that said light source has been used;

a computer memory for recording said actual amount of time that said light source has been used, said computer memory being in communication with said counting means; and a light source control for controlling a supply of power to said light source;

wherein said microcontroller is programmed to compare said actual amount of time that said light source has been used with a useful life of said light source, and wherein said light source control is adapted to receive a result of said comparison and to supply a reduced amount of power to said light source when said actual amount of time exceeds said useful life of said light source.

2. The lighting apparatus as claimed in claim 1 further comprising a display, said display being in communication with said microcontroller and being adapted to display said actual amount of time that said light source has been used.

3. The lighting apparatus as claimed in claim 2 wherein said display comprises at least one indicator light and wherein said microcontroller sends a number of signals to said indicator light, wherein said number of signals corresponds to a number of hours that said light source has been used, and wherein said indicator light is illuminated upon receipt of each of said signals.

4. The lighting apparatus as claimed in claim 3 wherein said display comprises three indicator lights, wherein said number of signals corresponds to a number of hundreds of hours, a number of tens of hours and a number of single hours, and wherein a first of said indicator lights is illuminated once for each signal corresponding to hundreds of hours, a second of said indicator lights is illuminated once for each signal corresponding to tens of hours, and a third of said indicator lights is illuminated once for each signal corresponding to single hours.

5. The lighting apparatus as claimed in claim 1 further comprising a temperature measurement device for measuring a temperature of said apparatus, wherein said temperature measurement device is in electrical communication with said light source control, and wherein said light source control is further adapted to control a supply of power to said light source based upon said temperature of said apparatus.

6. The lighting apparatus as claimed in claim 5 wherein said light source control comprises a light source control program within said microcontroller, and wherein said program is adapted to stop a supply of power to said light source when said temperature exceeds a predetermined temperature.

7. The lighting apparatus as claimed in claim 1 wherein said light source control program is adapted to start a supply of power to said light source after said apparatus is stopped and restarted.

8. The lighting apparatus as claimed in claim 1 wherein said microcontroller is further programmed to count and store a number of on/off cycles.

9. A lighting method for a lighting apparatus comprising a light source, said method comprising the steps of:

supplying power to said light source;

counting an actual amount of time that said power has been supplied to said light source;

comparing said actual amount of time that said power has been supplied to said light source with a useful life of said light source; and reducing a flow of power to said light source when said actual amount of time exceeds said a useful life of said apparatus.

10. The lighting method as claimed in claim 9 further comprising the step of displaying said actual amount of time that said power has been supplied to said light source.

11. The lighting method as claimed in claim 9 further comprising the step of measuring a temperature of said apparatus.

12. The lighting method as claimed in claim 9 further comprising the step of counting a number of on/off cycles of the apparatus.

13. A lighting apparatus comprising:

a light source;

a microcontroller;

counting means comprising a counting program within said microcontroller for counting an actual amount of time that said light source has been used;

a computer memory for recording said actual amount of time that said light source has been used, said computer memory being in communication with said counting means; and a light source control for controlling a supply of power to said light source;

wherein said microcontroller is programmed to compare said actual amount of time that said light source has been used with a useful life of said light source, and wherein said light source control is adapted to oscillate said power to said light source once said actual amount of time exceeds said useful life of said light source.

14. The lighting apparatus as claimed in claim 13 further comprising a display, said display being in communication with said microcontroller and being adapted to display said actual amount of time that said light source has been used.

15. The lighting apparatus as claimed in claim 14 wherein said display comprises at least one indictor light and wherein said microcontroller sends a number of signals to said indicator light, wherein said number of signals corresponds to a number of hours that said light source has been used, and wherein said indicator light is illuminated upon receipt of each of said signals.

16. The lighting apparatus as claimed in claim 15 wherein said display comprises three indicator lights, wherein said number of signals corresponds to a number of hundreds of hours, a number of tens of hours and a number of single hours, and wherein a first of said indicator lights is illuminated once for each signal corresponding to hundreds of hours, a second of said indicator lights is illuminated once for each signal corresponding to tens of hours, and a third of said indicator lights is illuminated once for each signal corresponding to single hours.

17. The lighting apparatus as claimed in claim 13 further comprising a temperature measurement device for measuring a temperature of said apparatus, wherein said temperature measurement device is in electrical communication with said light source control, and wherein said light source control is further adapted to control a supply of power to said light source based upon a said temperature of said apparatus.

18. The lighting apparatus as claimed in claim 13 wherein said microcontroller is further programmed to count and store a number of on/off cycles.

* * * * *